United States Patent [19]

Terao et al.

[11] Patent Number: 4,857,516
[45] Date of Patent: Aug. 15, 1989

[54] COUMARAN DERIVATIVES AND THEIR PHARMACEUTICAL USE

[75] Inventors: Shinji Terao, Osaka, Japan; Yoshitaka Maki, Highland Park, Ill.

[73] Assignee: Takeda Chemical Industries, Ltd., Osaka, Japan

[21] Appl. No.: 136,273

[22] Filed: Dec. 22, 1987

[30] Foreign Application Priority Data

Dec. 27, 1986 [JP] Japan ................................ 61-313380
Sep. 18, 1987 [JP] Japan ................................ 62-235491

[51] Int. Cl.$^4$ ..................... A61K 31/34; C07D 307/79
[52] U.S. Cl. .................................. 514/100; 514/320; 514/338; 514/365; 514/397; 514/462; 514/468; 514/469; 546/196; 546/269; 548/203; 548/204; 548/336; 549/220; 549/336; 549/457; 549/458; 549/462; 549/470
[58] Field of Search ............... 549/458, 462, 470, 336, 549/457, 220; 546/196, 269; 548/203, 204, 336; 514/100, 320, 338, 365, 397, 462, 468, 469

[56] References Cited

U.S. PATENT DOCUMENTS 2,421,811  6/1947  Smith et al. .................... 549/411

OTHER PUBLICATIONS

Smith et al., J.A.C.S. vol. 61, pp. 2615-2618 (1939).
Chemical Abstracts, vol. 72, No. 78857r, p. 384, 1970.
Chemical Abstracts, vol. 97, No. 38822e, pp. 569-570, 1982.
Chemical Abstracts, vol. 91, No. 140672z, p. 642, 1979.
Journal of the American Chemical Society, vol. 105, 1983, pp. 5950-5951.
Journal of the American Chemical Society, vol. 107, No. 24, 1985, "Autoxidation of Biological Molecules", pp. 7053-7065.

Primary Examiner—Mary C. Lee
Assistant Examiner—Bernard I. Dentz
Attorney, Agent, or Firm—Wegner & Bretschneider

[57] ABSTRACT

A compound of the formula

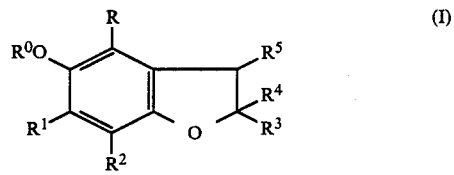

(I)

wherein R is a lower alkyl group, $R^0$ is hydrogen or an acyl group, $R^1$ and $R^2$ are lower alkyl groups which may optionally be substituted or wherein $R^1$ and $R^2$ are combined to form a butadienylene group which may optionally be substituted, $R^3$ and $R^4$ are hydrogen or alkyl groups which may optionally be substituted or wherein $R^3$ and $R^4$ are combined to form a polymethylene group, and $R^5$ is a lower alkyl, aromatic or heterocyclic group which may optionally be substituted or a pharmaceutically acceptable salt thereof, exerts cardiovascular system improving action and antiallergic action and can be used as pharmaceutics, e.g. antithromotics, antiallergic agents etc.

16 Claims, No Drawings

COUMARAN DERIVATIVES AND THEIR PHARMACEUTICAL USE

BACKGROUND AND PRIOR ART

This invention relates to new coumaran derivatives which are substituted at the 3-position.

More particularly, this invention relates to compounds of the formula

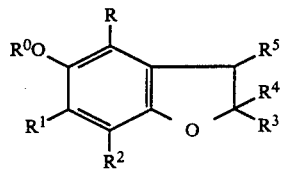

wherein R is a lower alkyl group, $R^0$ is hydrogen or an acyl group, $R^1$ and $R^2$ are lower alkyl groups which may optionally be substituted or wherein $R^1$ and $R^2$ are combined to form a butadienylene group which may optionally be substituted, $R^3$ and $R^4$ are hydrogen or alkyl groups which may optionally be substituted or wherein $R^3$ and $R^4$ are combined to form a polymethylene group; and $R^5$ is a lower alkyl, aromatic or heterocyclic group which may optionally be substituted, or pharmaceutically acceptable salts thereof.

Hitherto, related coumaran derivatives which are unsubstituted at the 3-position have been prepared and an antioxidant activity thereof are known [see J. Am. Chem. Soc., 105, 5950 (1983), ibid., 107, 7053 (1985)]. However, the above coumaran derivatives which are substituted at the 3-position as well as their phamaceutical activities have not been reported until now.

The present inventors succeeded in synthesizing various new coumaran derivatives which are substituted at the 3-position, and unexpectedly found that these compounds exert excellent pharmaceutical activities, such as cardiovascular system improving action and antiallergic action, e.g. scavenging action of active oxygen species which are produced in excess in living bodies, inhibition of thromboxane $A_2$ synthetase (thromboxane $A_2$ exerts coagulation of blood platelet as well as contraction of blood vessels) or inhibition or control of 5-lipoxygenase which is a key enzyme for the biosynthesis of leukotrienes.

Leukotrienes are potent chemical mediators for allergic or inflammatory reactions, and are considered to cause constriction of peripheral airways in the lung, being related to respiration distress accompanied by bronchial asthma. Also, leukotrienes possess the capabilities to enhance the capillary permeability and to strongly produce chemotactic activity of leukocytes and are intimately associated with edema and cellular infiltration, which are typical symptoms of inflammation.

BRIEF SUMMARY OF THE INVENTION

This invention provides the compound (I) or a pharmaceutically acceptable salt thereof, which exerts excellent cardiovascular system improving action or antiallergic action, such as scavenging action of active oxygen species, inhibition of thromboxane $A_2$ synthetase and inhibition of 5-lipoxygenase.

The compound (I) or a pharmaceutically acceptable salt thereof is useful as a pharmaceutical, such as a cardiovascular system improving agent and antiallergic agent etc.

DETAILED DESCRIPTION

In the above formula (I), the lower alkyl group of R, $R^1$, $R^2$, and $R^5$ is preferably a straight-chain or branched $C_{1-6}$alkyl group, such as methyl, ethyl, n-propyl, iso-propyl butyl, isobutyl, sec-butyl, t-butyl, pentyl or hexyl. The lower alkyl group of $R^1$, $R^2$ and $R^5$ may optionally be substituted by 1 to 3 groups exemplified by hydroxy, halogen, e.g. fluorine, chlorine, bromine or iodine, nitro, trifluoromethyl, carboxy, a $C_{1-3}$alkoxy-carbonyl group, e.g. methoxycarbonyl, ethoxycarbonyl or isopropoxycarbonyl, 3-pyridyl, 1-imidazolyl or 5-thiazolyl.

The acyl group of $R^0$ is an organic carboxylic acid acyl, sulfonic acid acyl or phosphoric acid acyl group and preferably contains substituents of 1 to 6 carbon atoms, such as methyl, ethyl, propyl or phenyl.

Examples of the acyl group include, among others, a $C_{1-10}$alkanoyl group, such as formyl, acetyl, propionyl, isobutyryl or decanoyl, a $C_{5-6}$cycloalkylcarbonyl group, such as cyclopentylcarbonyl or cyclohexylcarbonyl, benzoyl and a pyridinecarbonyl group, such as nicotinoyl, which may be made quaternary. The acyl group may also be carboxy $C_{2-6}$alkanoyl group, such as 3-carboxypropanoyl.

When $R^1$ and $R^2$ are combined to form a butadienylene group, the moiety:

forms a benzene ring or naphthalene ring moiety. These ring moieties may be susbtituted by a $C_{1-3}$alkyl group such as methyl or iso-propyl, a $C_{1-3}$alkoxy group such as methoxy, ethoxy or isopropoxy, hydroxy, oxo, nitro or halogen, the number of the substituents being 1 to 3.

The alkyl group of $R^3$ or $R^4$ is preferably a straight-chain or branched $C_{1-20}$alkyl group, such as methyl, ethyl, propyl, isopropyl, butyl, isobutyl, sec-butyl, tert-butyl, pentyl, hexyl, octyl, nonyl, decyl, undecyl, dodecyl, tridecyl, tetradecyl, pentadecyl, hexadecyl, heptadecyl, octadecyl, nonadecyl or eicosyl, more preferably a straight-chain or branched $C_{1-6}$alkyl group, such as methyl, ethyl, propyl, isopropyl, butyl, isobutyl, sec-butyl, tert-butyl, pentyl or hexyl. The alkyl group of $R^3$ or $R^4$ may optionally be substituted by 1 to 5 groups exemplified by (1) hydroxy, (2) carboxy, (3) a $C_{1-4}$alkoxy-carbonyl group, e.g. methoxycarbonyl, ethoxycarbonyl or butoxycarbonyl, (4) a $C_{6-14}$aryl group, such as phenyl, naphthyl or anthryl, preferably phenyl, which may be further sustituted by 1 to 5 groups exemplified by (a) hydroxy, (b) a $C_{1-3}$alkyl group, e.g. methyl, (c) halogen, e.g. fluorine or chlorine, (d) a $C_{1-3}$alkoxy group, e.g. methoxy, (e) carboxy, (f) trifluoromethyl, (5) 3-pyridyl, (6) 1-imidazolyl or (7) 5-thiazolyl.

When $R^3$ and $R^4$ are combined to form a polymethylene group, the moiety:

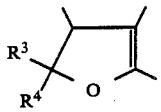

forms spiro-ring moiety. Preferable examples of the polymethylene group include a $C_{2-5}$alkylene group, such as ethylene, propylene, butylene or pentylene.

Examples of the aromatic group of $R^5$ include a $C_{6-14}$aryl group such as phenyl, 1- or 2-naphthyl and phenyl which are condensed with a cycloalkyl group (e.g. cyclopentyl or cyclohexyl), such as indanyl or tetralyl.

Examples of the heterocyclic group of $R^5$ include a 5-or 6-membered heterocyclic group containing 1 to 3 nitrogen atoms or/and 1 or 2 sulfur atoms, preferably 1 or 2 nitrogen atoms or/and 1 sulfur atom, such as 2- or 3-thienyl, 2-, 3-or 4-pyridyl, 1-imidazoyl or 5-thiazolyl. The heterocyclic group may be made quaternary at the ring-constituting nitrogen atom with a $C_{1-3}$alkyl group, e.g. methyl.

The aromatic or heterocyclic group of $R^5$ may optionally be substituted at an arbitrary position by 1 to 5, preferably 1 to 3 groups, such as (1) a straight-chain or branched $C_{1-20}$alkyl group, e.g. methyl, ethyl, propyl, isopropyl, butyl, t-butyl, pentyl, hexyl, octyl, nonyl, decyl, undecyl, dodecyl, tridecyl, tetradecyl, pentadecyl, hexadecyl, heptadecyl, octadecyl, nonadecyl or eicosyl, (2) a straight-chain or branched $C_{1-6}$alkyl group which is further substituted by hydroxy, carboxy, a $C_{1-4}$alkoxycarbonyl group, e.g. methoxycarbonyl or butoxycarbonyl, piperidinyl or phenylthio, (3) a $C_{2-4}$alkenyl group (e.g. vinyl) which may be further substituted by carboxy or or a $C_{1-6}$alkoxycarbonyl, (4) hydroxy, (5) halogen, e.g. fluorine, chlorine or bromine, (6) formyl, (7) a $C_{1-3}$alkoxy group, e.g. methoxy, ethoxy or isopropoxy, (8) carboxy, (9) trifluoromethyl, (10) a di-$C_{1-3}$alkylamino group, e.g. dimethylamino or dipropylamino, (11) a $C_{5-7}$cycloalkyl group, e.g. cyclopentyl or cyclohexyl or (12) a $C_{1-3}$alkylthio group, e.g. methylthio.

In the formula (I), preferably R is a $C_{1-3}$alkyl group, such as methyl, ethyl, n-propyl or isopropyl, $R^1$ and $R^2$ are straight-chain or branched $C_{1-6}$alkyl groups or $R^1$ and $R^2$ are combined to form a butadienylene group, $R^0$ is hydrogen or an organic carboxylic acid acyl group, $R^3$ and $R^4$ are straight-chain or branched $C_{1-6}$alkyl groups which may optionally be substituted by a $C_{6-14}$aryl group or $R^3$ and $R^4$ are combined to form a butylene or pentylene group, and $R^5$ is a 5- or 6-membered heterocyclic group containing 1 nitrogen atom which may optionally be made quaternary, or a $C_{6-14}$aryl group which may optionally be substituted by (1) a straight-chain or brancehd $C_{1-20}$alkyl group which is further substituted by carboxy, hydroxy, halogen, phenylthio or piperidinyl, the number of the substituents being 1 to 3, (2) a $C_{5-6}$cycloalkyl group, (3) a $C_{2-4}$alkenyl group which may be further substituted by carboxy, (4) hydroxy, (5) halogen, (6) formyl, (7) carboxy, (8) a di-$C_{1-3}$alkylamino group or (9) a $C_{1-3}$alkylthio group, the number of the substituents being 1 to 3, and said $C_{6-14}$aryl gorup may optionally be condensed with a $C_{5-6}$cyclaolkyl group.

More preferably R is methyl, $R^0$ is hydrogen, a $C_{1-10}$alkanoyl group or nicotinoyl, $R^1$ and $R^2$ are methyl or $R^1$ and $R^2$ are combined to form butadienylene, $R^3$ is methyl, $R^4$ is methyl, pentyl or benzyl or $R^3$ and $R^4$ are combeined to form butylene or pentylene, $R^5$ is (1) phenyl which may optionally be substituted by a straight-chain or branched $C_{1-20}$alkyl group, halogen, hydroxy or trifluoromethyl, the number of the substituents being 1 to 3, or (2) 2- or 3-pyridyl.

Especially preferred are compounds wherein R, $R^1$, $R^2$, $R^3$ and $R^4$ are straight-chain or branched $C_{1-6}$alkyl groups, e.g. methyl, $R^0$ is hydrogen, and $R^5$ is phenyl which is substituted by halogen or a straight-chain $C_{1-20}$alkyl group, the number of the substituents being 1 to 3, or phenyl which is condensed with a $C_{5-6}$cycloalkyl group.

When the compound (I) contains a basic group, such as dimethylamino, piperidinyl or pyridyl, the compound (I) may form an addition salt with an acid, e.g. conventional organic or inorganic acids, and when the compound (I) contains and acid group, such as carboxy, the compound may form a salt with a base, e.g. conventional organic or inorganic bases.

Examples of the pharmaceuticaly acceptable salt of compound (I) include an addition salt with an acid, such as an inorganic acid, e.g. hydrochloric acid, sulfuric acid or phosphoric acid, or an organic acid, e.g. citric acid, maleic aicd or malic acid, and a salt with a base, such as an inorganic base, e.g. sodium hydrogen carbonate, sodium carbonate, potassium carbonate, sodium hydroxide or potassium hydroxide, or an organic base, e.g. tertiary amine exemplified by trimethyalmino, triethylamino or pyridine.

The compound (I) or a pharmaceutically acceptable salt thereof can be produced by subjecting the compound of the formula

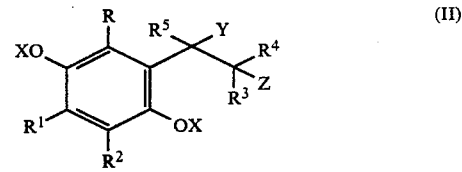

(II)

wherein X is hydrogen or a hydroxy-protecting group; and either of Y and Z is hydroxy and the other is hydrogen or Y and Z are combined to form a chemical bond, or a salt thereof, to ring-closure reaction in the presence of an acid catalyst, and, if desired, followed by acylation or/and convention reaction of a group of $R^5$.

As the hydroxy-protecting group of X, use may be made of protecting groups which are commonly used in a field of the organic synthesis.

Preferable examples of the hydroxy-protecting group of X include methyl, methoxymethyl, benzyl, tetrahydrofuranyl and trimethylsilyl.

As the acid catalyst, use is made of an inorganic acid, such as sulfuric acid, hydrochloric acid or hydrobromic acid.

The ring-closure reaction is usually conducted in a solvent. Examples of the solvent include water, acetic acid and aqueous acetic acid.

The reaction temperature is about 60° to 160° C. The reaction time is about 0.5 to 72 hours.

When the compound (II) contains a basic group, such as pyridyl or imidazolyl, the compound (II) may form an addition salt with an inorganic acid, such as hydrochloric acid, hydrobromic acid, sulfuric acid, nitric acid or phosphoric acid, or an organic acid, e.g. methansulfonic acid, p-toluenesulfonic acid or benzenesulfonic acid.

The protective group represented by X in the compound (II) can usually be removed by the acid catalyst during the ring-closure reaction. Therefore the deprotective reaction is usually unnecessary.

The hydroxy group at the 5-position of the compound (I) obtained or a salt thereof may converted into an acyloxy group by subjecting the compound (I) or a salt thereof to acylation, if desired.

The acylation is conducted by acylating the compound (I) wherein $R^0$ is hydrogen with an acylating agent, or a salt thereof. As the acylating agent, use may be made of conventional acylating agents, such as carboxylic anhydrides exemplified by acetic anhydride or propionic anhydride, or carboxylic acid halides exemplified by acetyl chloride.

The acylation is usually conducted in an organic solvent. Examples of the organic solvent include dimethylformamide, acetone or tetrahydrofuran. If necessary, catalyst, such as a base, e.g. an inorganic base exemplified by sodium hydride or potassium carbonate, or an organic base exemplified by pyridine or triethylamine; or an acid, preferably an inorganic acid, e.g. sulfuric acid or hydrochloric acid may be used in the reaction system.

The reaction temperature is usually about $-10°$ to $100°$ C. The reaction time is usually about 10 min. to 15 hours.

The group of $R^5$ in the compound (I) obtained or a salt thereof may be converted into another group, if desired. By the conversion reaction, for example, another substituent(s) can be introduced into the benzene ring of the phenyl group represented by $R^5$. In conducting the conversion reaction, when a group of the formula: $-OR^0$ is hydroxy, the hydroxy group may preferably be protected by a lower alkyl group, e.g. methyl.

For example, a phenyl group of $R^5$ can be converted into a formyl-substituted phenyl group by reacting with dichloromethylmethyl ether in the presence of a catalyst, such as titanium tetrachloride, and the formyl-substituted phenyl group can be converted into a hydroxymethyl-substituted phenyl group by a reduction reaction with a reducing agent, such as lithium aluminum hydride or sodium borohydride. The hydroxy-methyl-substituted phenyl group can be converted into a leaving group-substituted methylphenyl group, such as a halogeno-, tosyloxy- or mesyloxy-methylphenyl group by reacting with a halogenating agent, p-toluenesulfonyl chloride or methansulfonyl chloride respectively. The leaving group-substituted methylphenyl group can be converted into an amino-, phenylthio- or cyanomethylphenyl group by reaction with amine, thiophenol or sodium cyanide respectively.

The formyl-substituted phenyl group as mentioned above can be converted into a vinyl-substituted phenyl group by a Witting reaction of Knoevenagel reaction, and if necessary, followed by catalytic reduction using palladium carbon catalyst to convert a vinyl-substituted phenyl group into an alkyl-substituted phenyl group.

The protective group for the hydroxy group in the compound (I) obtained or a salt thereof may be removed in the presence of a catalyst, such as boron tribromide, protonic acid, e.g. hydrobromic acid or hydroiodic acid, or silicate compounds, e.g. trimethylsilyliodide (deprotective reaction).

The deprotective reaction is usually conducted in a solvent. Examples of the solvent include water, acetic acid, aqueous acetic acid, benzene, chloroform and carbon tetrachloride.

The reactin temperature is about $60°$ to $160°$ C. The reaction time is about 0.5 to 72 hours.

In the deprotective reaction, to hydrolyze functional group(s), such as cyano or ester at the same time, a protonic acid is preferably employed as the catalyst and an aqueous solvent is preferably employed as the solvent. In the case that boron tribromide or trimethylsilyl iodide is employed, a non-aqueous solvent, such as benzene or chloroform is usually employed. Futher, when an esterified carboxy is desired, it can be obtained by a conventional esterifying condition such as Fisher's reaction.

When the compound (I) is obtained in a free form, it may be converted into the pharmaceutically acceptable salt according to the conventional procedure, and vice versa.

The compound (I) obtained or a pharmaceutically acceptable salt thereof can be isolated and purified by conventional procedures, such as chromatography or recrystallization.

When the compound (I) or a pharmaceutically acceptable salt thereof is diastereoisomeric, each of the diastereoisomers can be isolated by the above conventional isolation and purification procedures.

When the compound (I) or a pharmaceutically acceptable salt thereof is optically active, the d- or l-form of the compound (I) or a pharmaceutically acceptable salt thereof can be isolated by conventional procedures, such as optical resolution.

The compound (I) or a pharmaceutically acceptable salt thereof exerts a therapeutic effect on the cardiovascular system and an antiallergic action, and specifically an improvement of the metablism of polyunsaturated fatty acids, e.g. linoleic acid, $\gamma$-linolenic acid, $\alpha$-linolenic acid, arachidonic acid, di-homo-$\gamma$-linolenic acid or eicosapentaenoic acid. Among these effects are particularly inhibition of production of lipid peroxide (antioxidation), inhibition of production of metabolites by 5-lipoxygenase system, e.g. leukotrienes, 5-hydroperoxyeicosatetraenoic acid (hereinafter referred to as HPETE), 5-hydroxyeicosatetraenoic acid (hereinafter referred to as HETE), lipoxins or leukotoxin, inhibition of thromboxane $A_2$ synthetase, maintenance and stimulation of prostagrandine $I_2$ synthetase, or scavenging action of active oxygen species. The compound (I) or a pharmaceutically acceptable salts thereof exerts two or more of these effect. Also the compound (I) or a pharmaceutically acceptable salt thereof is of low toxicity and has few side effects.

The compound (I) and its pharmaceutically acceptable salt thereof are expected to be effective for treatment and prevention of diseases in mammals, e.g. mouse, rat, rabbit, dog, monkey or human, such as thrombosis due to coagulation of blood platelet; ischemic diseases due to contraction or spasm of arterial smooth muscle in heart, lung, brain and kidney or due to contraction of blood vessels, e.g. myocardial infarction or cerebal stroke; chronic degenerative disorders, e.g. parkinsonism, Alzheimer's disease, Lou Gehrig's disease or muscular dystrophy; functional disorder, defects of memory and emotional disturbance due to central nervous system injury exemplified by head injury or spinal cord trauma (i.e. disorder caused by nerve cell death due to anoxia, cerebral injury, stroke, cerebral infarction or cerebral thrombosis); convulsions and epilepsy after stroke, cerebral infarction, cerebral surgery operation and head injury; nephritis; pulmonary failure; bronchial asthma; inflammation; arterioclerosis; atherosclerosis; hepatitis; immediate hepatits; cirrhosis of the liver; hypersensitivity pneumonitis; immunodeficiency; diseases of cardiovascular system due to disorder of enzymes, tissues and cells caused by active oxygen species exemplified by superoxides or hydroxide radicals, e.g. myocardial infarction, cerebral stroke, cerebral edema or nephritis; fibrosis; or cancer.

The compound (I) and its pharmaceutically acceptable salt can be used as pharmaceuticals, such as antithrombotic, anti-vasoconstrictve, antiallergic, antinephritic, anti-fibrositic, active oxygen-eliminating and arachidonate cascade control improving agents.

The compound (I) or a pharmaceutically acceptable salt thereof, or the pharmaceutical composition produced by mixing with a per se known, pharmaceutically acceptable carrier or excipient, such as tablets, capsules, liquid preparations, injections or suppositories, can be orally or parenterally given safely. The dose varies according to the subjects to be treated, the route of administration, symptoms, etc. For example, when given orally to an adult patient with diseases of cardiovascular system, the unit dose is usually about 0.1 mg/kg to 20 mg/kg body weight, preferably about 0.2 mg/kg to 10 mg/kg body weight which is desirably given about 1 to 3 times a day.

The starting compound (II) or a salt thereof can be produced by either of the following per se known methods A and B. For example, the compound (IIa) or a salt thereof can be produced by reacting the halogenocompound (III) or a salt thereof with n-butyllithium or metallic magnesium in a nonpolar solvent, such as diethyl ether or tetrahydrofuran, and reacting the resulting ketone compound (V) or a salt thereof [Method A]; or reacting the compound (IV) or a salt thereof with a Grignard reagent [Method B]. The compound (IIb) or salt thereof can be produced by subjecting the compound (IIa) or a salt thereof to dehydration reaction under heating in the presence of an acid catalyst, such as sulfuric acid, p-toluenesulfonic acid or benzenesulfonic acid. As the salt of compounds (III), (IV) and (V), use may be made of the same salt as in the compound (II).

Experiment 1

Inhibition of 5-lipoxygenase $10^7$ RBL-1 cells (rat basophilic leukemia cells) were suspended in 0.5 ml of MCM (mast cell medium). To the suspension was subsequently added a solution consisting of 0.5 ml of MCM, 50 $\mu$g of arachidonic acid and test compound (at the final concentration of 10 $\mu$M, 1 $\mu$M and 0.1 $\mu$M of the test compound) and reacted at 37° C. for 20 min. Then 4 ml of ethanol was added, and the mixture was well shaken and kept at room temperature for 10 min.

The mixture was centrifuged for 10 min. (2000 rpm), and the supernatant was separated. The supernatant obtained was concentrated to dryness under reduced pressure. To the residue 0.5 ml of 60 v/v % aqueous methanol was added. One hundred $\mu$l of this solution was subjected to high performance liquid chromatography for quantitative analysis of 5-HETE (5-hydroxyeicosatetraenoic acid). The amount of 5-HETE was determined by measurement of the absorbance at 237 nm with a UV absorption monitor.

The inhibitory effect (IE) of production of 5-HETE is expressed by $(1-b/a)\times 100$, wherein a is the peak height or the area corrected with the peak due to the internal standard in the absence of the compound (I) or a pharmaceutically acceptable salt thereof, and b is the peak height or peak area corrected with the peak due to the internal standard in the presence of the compound (I) or a pharmaceutically acceptable salt thereof.

The results demonstrate the potent inhibition of production of 5-HETE, as shown in Table 1.

TABLE 1

| Test compound | % Inhibition | | |
|---|---|---|---|
| (Example No.) | $10^{-6}$ M | $10^{-7}$ M | $10^{-8}$ M |
| 1 | 89 | 57 | 16 |
| 2 | 91 | 70 | 18 |
| 3 | 91 | 64 | 20 |
| 4 | 98 | 18 | 0 |
| 5 | 99 | 22 | 0 |
| 6 | 92 | 18 | 0 |
| 7 | 99 | 43 | 13 |
| 20 | 100 | 42 | 36 |

M; molecular concentration of the test compound

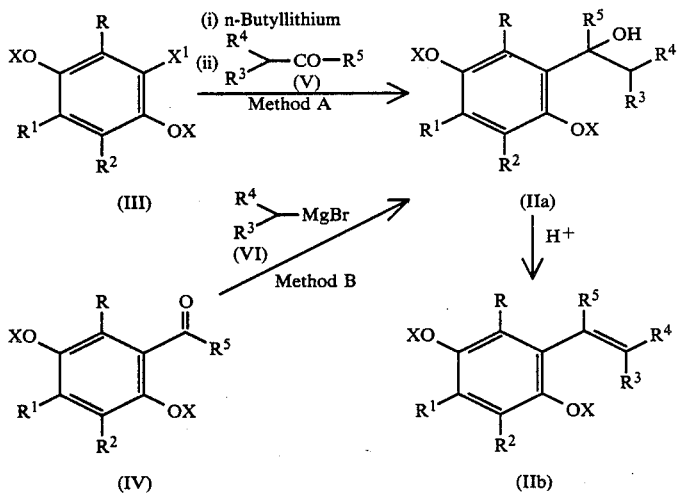

wherein $X^1$ is halogen, e.g. fluorine, chlorine, bromine or iodine and the other symbols are as defined above.

Experiment 2

Inhibitory effect on the generation of 12-hydroxyheptadeca-5,8,10-trienoic acid (HHT) in rat platelets Blood was collected in 3.2 v/v % sodium citrate (0.8 ml for 7.2 ml of blood) from the abdominal aorta of male Wister rats (Jcl, 12 to 15 weeks) anesthesized with pentobarbital. Platelet rich plasma (PRP) was obtained by centrifuging the blood at 800 rpm for 10 min at room temperature. Platelet poor plasma (PPP) was prepared by centrifuging the remaining blood at 3,000 rpm for 10 min. The platelet concentration of PRP was adjusted to 1,000,000/$\mu$l with PPP. 0.25 ml of PRP was incubated with arachidonic acid (125 $\mu$g) and the test compound (final conc.: 0.1, 1 and 10 $\mu$M) for 15 min. at 37° C.

The reaction was stopped by adding 100 ml of ethanol and the mixture was allowed to stand for 10 min. at room temperature. The reaction mixture was centrifuged at 2,000 rpm for 10 min. and the supernatant obtained was evaporated. To the concentrate, 0.2 ml of 60 v/v % aqueous ethanol was added.

100 $\mu$l of this solution was subjected to high performance liquid chromatography for quantitative analysis of HHT. The amount of HHT was determined by measurement of absorbance at 237 nm with a UV absorption monitor. The results are shown at Table 2.

The inhibitory effect (IE) on the generation of HHT is expressed by $(1-b/a) \times 100$, wherein a is the peak height or the peak area corrected with the peak due to the internal standard in the absence of the compound (I) or a pharmaceutically acceptable salt thereof, and b is the peak height or the peak area corrected with the peak due to the internal standard in the compound (I) or a pharmaceutically acceptable salt thereof.

TABLE 2

| Test compound | % inhibition | |
| (Example No.) | $10^{-4}$ M | $10^{-5}$ M |
| --- | --- | --- |
| 1 | 76 | 47 |
| 2 | 79 | 52 |
| 3 | 40 | 7 |
| 4 | 29 | 9 |
| 5 | 84 | 54 |
| 6 | 49 | 7 |
| 7 | 49 | 35 |

M: molecular concentration of the test compound

Experiment 3

Inhibitory action on lipid peroxide production in rat brain homogenates

The male SD rat (12 weeks) brain tissue was extracted under anesthesia after depletion. The extracted brain tissue was used as 5 v/v % homogenate in phosphate buffer (pH 7.4). After incubation of the homogenate for 1 hour at 37° C., the peroxide produced was determined by the thiobarbituric acid method according to the method described in Analytical Biochemistry, 95, 551 (1979).

Before incubation, test compounds were added in 5 v/v % homogenate so that their final concentration becomes $10^{-5}$ M.

The results are shown in Table 3. The inhibitory action on lipid peroxide production is expressed as a % inhibition as compared with the amount of production in the vehicle (dimethlysulfoxide) group.

TABLE 3

| Test compound (Example No.) | Inhibition (IC$_{50}$) $\times 10^{-7}$ |
| --- | --- |
| 1 | 2.2 |
| 2 | 7.5 |
| 3 | 1.5 |
| 4 | 2.5 |
| 5 | 1.2 |
| 6 | 1.3 |
| 7 | 2.3 |
| 20 | 0.25 |

Experiment 4

Effects of drugs on the excitatory behavior induced by spinal intrathecal injection of FeCl$_2$ in mice Male Slc:ICP mice (5 weeks) were used. Each group consisted of 10 mice. 5 $\mu$l of 50 mM FeCl$_2$ in saline was injected into spinal subarchnoid space betwen the 1st sacral and the 6th lumbar segment, the behavioral responses were observed from 15 min. to 1 hr. after the intrathecal injection of FeCl$_2$ and scored as follows.

Score    Behavioral responses
0: normal (no abnormal behavior)
1: vigorously biting lower abdomen or lower extremities
2:
  (a) extremely biting lower body with rolling
  (b) hyperreactivity and agressive to external stmuli
  (c) tremor
  at least one of above three behavioral changes were observed
3: clonic convulsion
4: tonic convulsion or paralysis of lower extremities.
5: death The test compounds (100 mg/kg) were orally administered 30 min. prior to FeCl$_2$ injection. The mean scores and their percent inhibitions are shown in Table 4(I).

TABLE 4 (I)

| Test compound | Score | | Percent |
| (Example No.) | 100 mg/kg p.o. | Vehicle p.o. | inhibition |
| --- | --- | --- | --- |
| 7 | 0.3 | 4.2 | 93 |
| 11 | 0.7 | 4.5 | 84 |
| 13 | 0.7 | 4.2 | 83 |

Experiment 5

Effect on the neurological deficits in rats with experimental cerebral ischemia Male Crj:Wistar rats, that were 7 weeks old at the time of electocauterization of the bilateral vertebral arteries, were used. Electrocauterization of the bilateral vertebral arteries was performed under pentobarbital Na (40 mg/kg, i.p.) anesthesia. Global cerebral ischemia was produced by 20 min. occlusion of both common carotid arteries 24 hr after the permanent electrocauterization of the bilateral vertebral arteries (Pulsinelli W. A. and Brierly J. B., Stroke 10, 267–272 (1979)).

The compound of Example 20 was given orally as a single dose immediately after the reperfusion of both carotid arteries. The neurological deficits caused by transient cerebral ischemia were observed for 14 days and were graded according to the following scores:
0; normal 1; decrease in spontaneous motor activity, piloerection, ptosis, miosis, hyperirritability, slight ataxia
2; moderate to servere ataxia
3; loss of righting reflex, slight convulsions
4; severe convulsions, coma
5; death The median neurological deficit scores of the drug-treated groups were compared with that of saline-treated control. Statistical analysis was done using the Mann-Whitney U-test.

TABLE 4 (II)

Effect of the compound of Example 20 on neurological deficits in rats with cerebral ischemia (median value)

| Test compound | Days # | | | | | | |
|---|---|---|---|---|---|---|---|
| | 1 | 2 | 3 | 5 | 7 | 10 | 14 |
| Saline | 2 | 2 | 2 | 2 | 2 | 1 | 0 |
| Compound of Example 20 | | | | | | | |
| 10 mg/kg, p.o. | 2 | 2 | 1.5* | 1** | 1* | 0** | 0 |
| 40 mg/kg, p.o. | 2 | 2 | 1** | 1** | 1* | 0* | |

Days mean days after cerebral ischemia
*p < 0.05,
**p < 0.01 (Mann-Whitney U-test)

The compound of Example 20 (10 and 40 mg/kg, p.o.) significantly ameliorated the neurological deficits caused by transient cerebral ischemia in rats.

Experiment 6

Effect on functional neutologic impairment induced by spinal cord compression in rats Male Jcl:Wistar rats, weighing about 350 g at the time of spinal cord compression were used. A spinal cord injury was produced in rats by compressing the spinal cord with a stainless screw of 2.8 mm length and 2 mm diameter at thoracic 11 (T11) level under pentobarbital anesthesia. On the day of the operation, the screw was placed so that the end was just above the subarachnoid membrane of the spinal cord.

On the following day, the screw was completely tightened to compress the spinal cord without penetrating the subarachnoid membrane. After compression of the spinal cord for 60 min., the screw was removed. Test compounds were given orally 5 min. after the removal of screw. The neurologic impairment was observed for 14 days and was graded according to the following score:

0; flaccid paralysis, no movement of hind limbs, no response to pinching of tail with foreceps (i.e. movement of fore limbs, biting foreceps, vocalization)
1; no movement of hind limbs, but responds to pinching of tail with foreceps
2; uncoordinated movement (loss of coordination between limbs), but can not support own weight
3; movement with an impairment (general coordination between limbs), but can not support own weight
4; walking with a slight ataxia of the hind limbs, but can support own weight
5; normal gait.

The median neurological score of the drug-treated groups were compared with that saline-teated control group. Statistical analysis was done using the Mann-Whitney U-test. The incidence of rats showing urinary incontinence was also compared by the $\chi^2$-test.

TABLE 4 (III)

Effects of compounds of Examples 7 and 20 on neurological deficits caused by spinal cord compression in rats (median value)

| Test compound | Days | | | |
|---|---|---|---|---|
| | 1 | 3 | 7 | 14 |
| Saline | 1 | 2 | 2 | 4 |
| Compound of Ex. 7 (40 mg/kg, p.o.) | 2 | 2* | 3 | 4 |
| Compound of Ex. 20 (40 mg/kg, p.o.) | 2** | 3** | 4** | 4* |

*p < 0.05,
**p < 0.01 vs. saline control (Mann-Whitney U-test)

TABLE 4 (IV)

Incidence of rats showing urinary incontinence

| Test compound | Days | | | | | | |
|---|---|---|---|---|---|---|---|
| | 1 | 2 | 3 | 5 | 7 | 10 | 14 |
| Saline | 57.1 | 57.1 | 57.1 | 50.0 | 42.9 | 28.6 | 28.6 |
| Compound of Ex. 7 (40 mg/kg, p.o) | 42.9 | 14.3 | 7.1* | 7.1 | 0* | 0 | 0 |
| Compound of Ex. 20 (40 mg/kg, p.o.) | 0** | 0** | 0** | 0** | 7.1 | 7.1 | 7.1 |

*p < 0.05,
**p < 0.01 vs. saline control

As shown in Tables 4(III) and 4(IV), the compounds of Examples 7 and 20 ameliorated the neurological impairment caused by spinal cord compression, and also reduced the incidence of urinary incontinence.

Reference Example 1

To a solution of 11.4 g (200 mmol) of propylenimine and 28.9 ml (207 mmol) of triethylamine in 250 ml of petroleum ether was added 20.2 g (190 mmol) of isobutyryl chloride at 0° C. while stirring. After stirring at 0° C. for 1 further hour, the precipitating triethylamine hydrochloride was filtered out and the filtrate obtained was evaporated under reduced pressure. The residue was distilled under reduced pressure to obtain 14.5 g (yield: 61%) of N-isobutyrylpropylenimine showing bp. 56°–58° C./13 mmHg.

According to the same procedure as above, N-cyclohexanecarbonylpropylenimine (yield: 80%, bp. 70°–72° C/12 mmHg) and N-cyclopentanecarbonylpropylenimine (yield: 88%, bp. 60°–62° C./4 mmHg) were obtained.

Reference Example 2

A solution of 10.0 g (63.3 mmol) of 3-bromopyridine in 100 ml of ethyl ether was cooled to $-78°$ C., to which was added dropwise 39.6 ml (163.3 mmol) of 1.6 M n-butyllithium-hexane solution, followed by stirring at the same temperature for 20 min. To the mixture was added dropwise 8.04 g (63.3 mmol) of N-isobutyrylpropylenimine, and it was stirred at room temperature for 1 hour.

To the reaction mixture was added water, and it was extracted with ethyl acetate. The extracts were washed with water, dried over magnesium sulfate and concentrated. The residue was distilled under reduced pressure to obtain 7.0 g (yield: 74.2%) of 3-isobutyrylpyridine showing bp. 70°–71° C./2 mmHg.

According to the same procedure as above, the following compounds were obtained:
3-(cyclohexylcarbonyl)pyridine
  yield 75.2%, bp. 138°–140° C./5 mmHg
3-(cyclopentylcarbonyl)pyridine yield 70.4%, bp. 98°–100° C./2 mmHg
2-isobutyrylpyridine
  yield 62.0%
4-bromophenylcylcopentylketone
  yield 72.8%
1-(1-naphthyl)-2-methylpropanone
  yield 75.9%
1-[4-(N-dimethylamino)phenyl]-2-methylpropanone
  yield 77.7%
1-(3-methoxyphenyl)-2-methylpropanone
  yield 90.0%
1-(3,4-dimethylphenyl)-2-methylpropanone
  yield 75.9%
1-(2,4-dimethylphenyl)-2-methylpropanone
  yield 67.6%
1-(4-bromophenyl)-2-methylpropanone
  yield 89.7%.

Reference Example 3

14.0 g (105 mmol) of anhydrous aluminum chloride was suspended in a mixture of 14.4 g (150 mmol) of fluorobenzene and 15 ml of carbon disulfide, to which was added dropwise 10.6 g (100 mmol) of isobutyryl chloride under cooling and stirring. After stirring for further 15 min., the reaction mixture was poured into ice-water and extracted with isopropyl ether. The extracts were washed, dried and evaporated under reduced pressure.

Distillation of the residue under reduced pressure gave 9.3 g (yield: 56.3%) of 1-(4-fluorophenyl)-2-methylpropanone showing bp. 105°–110° C./20 mmHg.

According to the same procedure as above, the following compounds were obtained.
1-(4-chlorophenyl)-2-methylpropanone
  yield 48%
1-(4-methylphenyl)-2-methylpropanone
  yield 88.6%, bp. 130°–133° C./26 mmHg
1-(4-ethylphenyl)-2-methylpropanone
  yield 70.0%, bp. 135°–138° C./22 mmHg
1-(4-propylphenyl)-2-methylpropanone
  yield 66.1%, bp. 145°–148° C./17 mmHg
1-(4-isopropylphenyl)-2-methylpropanone
  yield 90.5%, bp. 130°–134° C./15 mmHg
1-(4-amylphenyl)-2-methylpropanone
  yield 94.0%, bp. 125°–128° C./4 mmHg
1-(4-octylphenyl)-2-methylpropanone
  yield 84.6%, bp. 160°–163° C./5 mmHg
1-(4-decylphenyl)-2-methylpropanone
  yield 91.0%
1-(4-dodecylphenyl)-2-methylpropanone
  yield 88.8%
1-(4-tetradecylphenyl)-2-methylpropanone
  yield 93.7%
1-(4-hexadecylphenyl)-2-methylpropanone
  yield 94.3%, mp 29°–30° C.
1-(4-octadecylphenyl)-2-methylpropanone
  yield 88.7%, mp 38°–39° C.
1-(4methoxyphenyl)-2-methylpropanone
  yield 87.4%, bp. 145°–148° C./16 mmHg
1-[4-(methylthio)phenyl]-2-methylpropanone
  yield 46.9%, bp. 120°–121° C./2 mmHg
1-(5-indanyl)-2-methylpropanone
  yield 73.9%, bp. 113°–115° C./4 mmHg
1-(4-cyclohexylphenyl)-2 -methylpropanone
  yield 84.1%, bp. 143°–145° C./2 mmHg
1-(5,6,7,8-tetrahydro-2-naphthyl)-2-methylpropanone
  yield 43.0%,
1-(4-t-butylphenyl)-2-methylpropanone
  yield 64.0%, bp. 137°–140° C./17 mmHg Reference Example 4

To a solution of 3.0 g (19.7 mmol) of 1-(4-fluorophenyl)propanone and 3.9 g (19.7 mmol) of 1-iodopentane in 20 ml of dimethylformamide was added 0.95 g (23.6 mmol) of sodium hydride (content: 60 w/w %) and the mixture was stirred at 60° C. for 30 min. The reaction mixture was diluted with water and extracted with isopropyl ether. The extracts were washed, dried and concentrated, and the resultant residue was chromatographed on a column of silica gel, elution being conducted with isopropyl ether-hexane (5:95 v/v) to obtain 3.1 g (yield: 70.8%) of 1-(4-fluorophenyl)-2-methylheptanone.

According to the same procedure as above, 1-(4-fluorophenyl)-2-benzylpropanone (yield: 52.3%) was obtained.

Reference Example 5

To an isopropyl magnesium bromide solution prepared from 7.9 g (45.4 mmol) of 2-bromopropane, 1.47 g of magnesium and 60 ml of tetrahydrofuran was added dropwise a solution of 10.0 g (57.4 mmol) of 4-trifluoromethylbenzaldehyde in 10 ml of tetrahydrofuran at 0° C. while stirring.

The reaction mixture was stirred at room temperature for 1 further hour, and water was added to the reaction mixture so that the reaction stopped. The reaction mixture was extracted with ethyl acetate and the extracts were washed with water, dried and concentrated. The residue was chromatographed on a column of silica gel, elution being conducted with hexane-isopropyl ether (2:1 v/v) to obtain 5.0 g (yield: 39.9%) of 1-(4-trifluoromethylphenyl)-2-methylpropanol.

According to the same procedure as above, the following compounds were obtained:
1-(2-fluorophenyl)-2-methylpropanol
  yield 17.7%
1-(3-fluorophenyl)-2-methylpropanol
  yield 20.6%
1-(2-naphthyl)-2-methylpropanol
  yield 41.3%.

Reference Example 6

In 20 ml of acetone was dissolved 3.7 g of 1-(4-trifluoromethylphenyl)-2-methylpropanol obtained in Reference Example 5, to which was added dropwise Jones' reagent until the red color of the solution caused by Jones' reagent does not disappear. The reaction mixture was diluted with water and extracted with isopropyl ether. The extracts were washed with water, dried and concentrated.

The residue was chromatographed on a column of silica gel, the elution being conducted with hexane-isopropyl ether (9:1 v/v), to obtain 2.75 g (yield: 75.0%) of 1-(4-trifluoromethylphenyl)-2-methylpropanone.

According to the same procedure as above, the following compounds were obtained:
1-(2-fluorophenyl)-2-methylpropanone, yield 84.0%
1-(3-fluorophenyl)-2-methylpropanone, yield 66.5%
1-(2-naphthyl)-2-methylpropanone, yield 71.7%.

Reference Example 7

To a solution of 3.0 g (11.6 mmol) of 1-bromo-2,5-dimethoxy-3,4,6-trimethylbenzene in 30 ml of tetrahydrofuran, which was cooled to −78° C., was added dropwise 7.25 ml (11.6 mmol) of 1.6 M n-butyllithiumn-hexane solution while stirring. After stirring at the same temperature for 20 min., a solution of 1.64 g (11.0 mmol) of 3-isobutyrylpyridine in 5 ml of tetrahydrofuran was added dropwise to the reaction mixture.

The reaction mixture was stirred at room temperature for 1 hour, then water was added, and the mixture was extracted with ethyl acetate. The extracts were back-extracted with 2N-hydrochloric acid and the water layer obtained was made weakly alkaline by sodium hydrogen carbonate. This was followed by extraction with ethyl acetate. The extracts were washed, dried and concentrated. Crystallization of the residue from ethyl acetate-isopropyl ether gave 2.93 g of 1-(2,5-dimethoxy-3,4,6-trimethylphenyl)-1-(3-pyridyl)-2-methylpropanol.

According to the procedure as above, the following compounds were obtained:

2,5-dimethoxy-3,4,6-trimethylphenyl-(3-pyridyl)cyclohexylmethanol, yield 88%, mp. 134°–135° C.
2,5-dimethoxy-3,4,6-trimethylphenyl-(3-pyridyl)cyclopentylmethanol, yield 80%, mp. 126°–127° C.
1-(1,4-dimethoxy-3-methyl-2-naphtyl)-1-(3-pyridyl)-2-methylpropanol, yield 80%, mp. 130°–131° C.
1-(2,5-dimethoxy-3,4,6-trimethylphenyl)-1-(2-pyridyl)-2-methylpropanol, yield 89%, mp. 99°–100° C.

Reference Example 8

To a solution of 3.0 g (11.6 mmol) of 1-bromo-2,5-dimethoxy-3,4,6-trimethylbenzene in 30 ml of tetrahydrofuran, which was cooled to −78° C., was added dropwise 7.25 ml (11.6 mmol) of 1.6 M n-butyllithium-n-hexane solution while stirring. After stirring at the same temperature for 20 min., a solution of 1.9 g (11.4 mmol) of 1-(4-fluorophenyl)-2-methylpropane in 5 ml of tetrahydrofuran was added dropwise to the reaction mixture.

The reaction mixture was stirred at room temperature for 1 further hour, and to the reaction mixture was added water. This was followed by extraction with ethyl acetate. The extracts were washed with water, dried and concentrated.

Crystallization of the resulting residue gave 3.7 g (yield: 92.3%) of 1-(4-fluorophenyl)-1-(2,5-dimethoxy-3,4,6-trimethylphenyl)-2-methylpropanol showing mp. 129°–130° C.

According to the same procedure as above the following compound were obtained:

1-(2,5-dimethoxy-3,4,6-trimethylphenyl)-1-phenyl-2-methylpropanol
yield 90.8%, mp. 90°–91° C.
1-(1,4-dimethoxy-3-methyl-2-naphthyl)-1-(4-fluorophenyl)-2-methylpropanol
yield 81%, an oil
1-(2,5-dimethoxy-3,4,6-trimethylphenyl)-1-(4-bromophenyl)-2-methylpropanol
yield 75%, mp. 157°–158° C.
1-(2,5-dimethoxy-3,4,6-trimethylphenyl)-1-(4-chlorophenyl)-2-methylpropanol
yield 70%, mp. 149°–150° C.
4-bromophenyl-2,5-dimethoxy-3,4,6-trimethylphenyl-cyclohexylmethanol
yield 85%, mp. 130°–131° C.
1-(4-fluorophenyl)-1-(2,5-dimethoxy-3,4,6-trimethylphenyl)-2-methylheptanol
yield 83%, a mixture of diasteroisomers
1-(2,5-dimethoxy-3,4,6-trimethylphenyl)-1-(4-fluorophenyl)-2-methyl-3-phenylpropanol
yield 87%, a mixture of diasteroisomers
1-(2,5-dimethoxy-3,4,6-trimethylphenyl)-1-(4-trifluoromethylphenyl)-2-methylpropanol
yield 89%, mp. 154°–155° C.
1-(2-fluorophenyl)-1-(2,5-dimethoxy-3,4,6-trimethylphenyl)-2-methylpropanol
yield 68.4%, mp. 84°–85° C.
1-(3-fluorophenyl)-1-(2,5-dimethoxy-3,4,6-trimethylphenyl)-2-methylpropanol
yield 88.1%, mp. 83°–84° C.
1-(4-methylphenyl)-1-(2,5-dimethoxy-3,4,6-trimethylphenyl)-2-methylpropanol
yield 63.1%, mp. 153°–154° C.
1-(4-ethylphenyl)-1-(2,5-dimethoxy-3,4,6-trimethylphenyl)-2-methylpropanol
yield 60.6%, mp. 132°–133° C.
1-(4-propylphenyl)-1-(2,5-dimethoxy-3,4,6-trimethylphenyl)-2-methylpropanol
yield 70.0%, mp. 94°–95° C.
1-(4-isopropylphenyl)-1-(2,5-dimethoxy-3,4,6-trimethylphenyl)-2-methylpropanol
yield 81.7%, mp. 127°–128° C.
1-(4-amylphenyl)-1-(2,5-dimethoxy-3,4,6-trimethylphenyl)-2-methylpropanol
yield 78.9%, mp. 86°–87° C.
1-(4-octylphenyl)-1-(2,5-dimethoxy-3,4,6-trimethylphenyl)-2-methylpropanol
yield 68.9%, mp. 60°–61° C.
1-(4-decylpheny)-1-(2,5-dimethyl-3,4,6-trimethylphenyl)-2-metylpropanol
yield 88.5%, mp. 71°–72° C.
1-(4-dodecylphenyl)-1-(2,5-dimethoxy-3,4,6-trimethylphenyl)-2-methylpropanol
yield 83.7%, mp. 51°–52° C.
1-(2,5-dimethoxy-3,4,6-trimethylphenyl)-1-(4-tetradecylphenyl)-2-methylpropanol
yield 88.4%, mp. 54°–55° C.
1-(4-hexadecylphenyl)-1-(2,5-dimethoxy-3,4,6-trimethylphenyl)-2-methylpropanol
yield 86.0%, mp. 64°–65° C.
1-(4-octadecylphenyl)-1-(2,5-dimethoxy-3,4,6-trimethylphenyl)-2-methylpropanol
yield 83.2%, mp. 69°–70° C.
1-(4-methoxyphenyl)-1-(2,5-dimethoxy-3,4,6-trimethylphenyl)-2-methylpropanol
yield 62.5%, mp. 156°–157° C.
1-(4-t-butylphenyl)-1-(2,5-dimethoxy-3,4,6-trimethylphenyl)-2-methylpropanol
yield 64.0%, mp. 146°–147° C.
1-(3-methoxyphenyl)-1-(2,5-dimethoxy-3,4,6-trimethylphenyl)-2-methylpropanol
yield 69.8%, mp. 119°–120° C.
1-[4-(methylthio)phenyl]-1-(2,5-dimethoxy-3,4,6-trimethylphenyl)-2-methylpropanol
yield 81.0%, mp. 124°–125° C.
1-(2,4-dimethylphenyl)-1-(2,5-dimethoxy-3,4,6-trimethylphenyl)-2-methylpropanol
yield 56.3%, an oil
1-(3,4-dimethylphenyl)-1-(2,5-dimethoxy-3,4,6trimethylphenyl)-2-methylpropanol
yield 51.6%, mp. 169°–170° C.
1-(5-indanyl)-1-(2,5-dimethoxy-3,4,6-trimethylphenyl)-2-methylpropanol
yield 85.4%, mp 108°–109° C.
1-[6-(1,2,3,4-tetrahydronaphtyl)]-1-(2,5-dimethoxy-3,4,6-trimethylphenyl)-2-methylpropanol
yield 77.1%, mp. 117°–118° C.
1-(4-cyclohexylphenyl)-1-(2,5-dimethoxy-3,4,6-trimethylphenyl)-2-methylpropanol yield 75.1%, mp. 119°–120° C.
1-(1-naphtyl)-1-(2,5-dimethoxy-3,4,6-trimethylphenyl)-2-methylpropanol
yield 52.6%, mp. 134°–135° C.
1-(2-napthyl)-1-(2,5-dimethoxy-3,4,6-trimethylphenyl)-2-methylpropanol
yield 64.9%, mp. 130°–131° C.
1-[4-(dimethylamino)phenyl]-2,5-dimethoxy-3,4,6-trimethylphenyl-2-methylpropanol
yield 51.6%, mp. 169°–170° C.

Reference Example 9

In 20 ml of acetic acid was dissolved 1.3 g (3.5 mmol) of 2,5-dimethoxy-3,4,6-trimethylphenyl-(3-pridyl)cyclohexylmethanol, to which was added 1.3 ml of conc. sulfuric acid, followed by heating at 80° C. for 1 hour. After cooling to room temperature, the reaction mixture was neutralized with sodium hydrogen carbonate and extracted with ethyl acetate.

The extracts were washed with water, dried and concentrated. Crystallization of the residue from isopropyl ether-hexane gave 1.2 g (yield: 97%) of 3-[(2,5-dimethoxy-3,4,6-trimethylphenyl)cyclohexylidenemethyl]pyridine.

mp. 144°–145° C.

Reference Example 10

In 100 ml of dimethylforamide was dissolved 13.6 g (48.2 mmol) of 5-hydroxy-2,2,4,6,7-pentamethyl-3-phenyl-2,3-dihydrobenzofuran, obtained in Example 6, to which was added 2.3 g (58 mmol) of sodium hydride (content: 60 w/w %) in small portions at 0° C. while stirring.

After stirring for 30 min., 7.5 g (53.0 mmol) of methyl iodide was added to the reaction mixture and stirred at room temperature for 30 min. To the reaction mixture was added water, followed by extract with isopropyl ether. The extracts were washed with water, dried and concentrated.

Crystallization of the residue from hexane-isopropyl ether gave 13.5 g (yield: 94.6%) of 5-methoxy-2,2,4,6,7-pentamethyl-3-phenyl-2,3-dihydrobenzofuran.

mp. 100°–101° C.

According to the same procedure as above, 3-(4-bromophenyl)-5-methoxymethyloxy-2,2,4,6,7-pentamethyl-2,3-dihydrobenzofuran was obtained, using chloromethyl ether as an alkylating agent.

Yield: 95.1%

Reference Example 11

In 25 ml (41.6 mmol) of methylene chloride were dissolved 12.3 g (41.6 mmol) of 5-methoxy-2,2,4,6,7-pentamethyl-3-phenyl-2,3-dihydrobenzofuran, obtained in Reference Example 10, and 5.0 g (45.8 mmol) of 1,1-dichloromethyl methyl ether, to which was added dropwise 13.5 ml (123 mmol) of titanium tetrachloride under stirring and cooling, followed by refluxing for 2 hours. After cooling to room temperature, the reaction mixture was poured into ice-water.

The organic layer was separated and washed with water and a saturated aqueous sodium hydrogen carbonate solution in that order, then dried and concentrated.

Recrystallization of the residue from isopropyl ether-hexane gave 10.0 g (yield: 74.3%) of 3-(4-formylphenyl)-5-methoxy-2,2,4,6,7-pentamethyl-2,3-dihydrobenzofuran.

mp. 108°–109° C.

Reference Example 12

In 5 ml of ethanol was dissolved 1.0 g (3.1 mmol) of 3-(4-formylphenyl)-5-methoxy-2,2,4,6,7-pentamethyl-2,3-dihydrobenzofuran, obtained in Reference Example 11, to which 58.4 mg (1.55 mmol) of sodium borohydride was added under stirring and cooling. After stirring for 30 min., the reaction mixture was diluted with water, and extracted with isopropyl ether. The extracts were washed with water, dried and concentrated.

Crystallization of the residue from isopropyl ether gave 0.82 g (yield: 81.5%) of 3-[4-(hydroxylmethyl)phenyl]-5-methoxy-2,2,4,6,7-pentamethyl-2,3-dihydrobenzofuran.

mp. 65°–66° C.

Reference Example 13

In 40 ml of isopropyl ether was dissolved 4.0 g (12.3 mmol) of 3-[4-(hydroxymethyl)phenyl]-5-methoxy-2,2,4,6,7-pentamethyl-2,3-dihydrobenzofuran obtained in Reference Example 12, to which 2.2 g of phosphorus tribromide was added dropwise under cooling and stirring. After stirring for 30 min. The reaction mixture was washed with water and aqueous sodium hydrogen carbonate solution in that order, then dried and concentrated.

Recrystallization of the residue from hexane gave 3.0 g (yield: 62.9%) of 3-[4-(bromomethyl)phenyl]-5-methoxy-2,2,4,6,7-pentamethyl-2,3-dihydrobenzofuran.

mp. 97°–98° C.

Reference Example 14

To 10 ml of dimethylsulfoxide were added 1.1 g (2.8 mmol) of 3-[4-(bromomethyl)phenyl]-5-methoxy-2,2,4,6,7-pentamethyl-2,3-dihydrobenzofuran obtained in Reference Example 13 and 206 mg (4.2 mmol) of sodium cyanide, which was stirred at 80° C. for 1 hour. The reaction mixture was diluted with water and extracted with isopropyl ether. The extract was concentrated under reduced pressure.

The residue was chromatographed on a column of silica gel, elution being conducted with hexane-isopropyl ether (8:2 v/v) to obtain 0.9 g (yield: 95.0%) of 3-[4-(cyanomethyl)phenyl]-5-methoxy-2,2,4,6,7-pentamethyl-2,3-dihydrobenzofuran.

Reference Example 15

In 10 ml of dimethylformamide was dissolved 0.56 g (6.8 mmol) of thiophenol, to which 240 mg (6 mmol) of sodium hydride (content: 60 w/w %) was added under cooling and stirring. To the mixture was added a solution of 0.56 g (1.45 mmol) of 3-(4-(bromomethyl)phenyl]-5-methoxy-2,2,4,6,7-pentamethyl-2,3 -dihydrobenzofuran, obtained in Reference Example 13, in 5 ml of dimethylformamide, and the mixture was stirred at room temperature for 30 min.

The reaction mixture was diluted with water and extracted with isopropyl ether. The extracts obtained were dried and concentrated.

Crystallization of the residue from hexane-isopropyl ether gave 1.28 g (yield: 60.9%) of 3-[4-(phenylthiomethyl)phenyl]-5-methoxy-2,2,4,6,7-pentamethyl-2,3-dihydrobenzofuran.

mp. 91°–92° C.

According to the same manner as above, 3-[4-(piperidinomethyl)phenyl]-5-methoxy-2,2,4,6,7-pentamethyl-2,3-dihydrobenzofuran was obtained. Yield: 56.3%

Reference Example 16

A mixture of 2.0 g of 3-(4-formylphenyl)-5-methoxy-2,2,4,6,7-pentamethyl-2,3-dihydrobenzofuran, obtained in Reference Example 11, 2.82 g (6.17 mmol) of 5-carboxypentyl triphenylphosphonium bromide, 543 mg (13.6 mmol) of sodium hydride, 3 ml of dimethylsulfoxide and 5 ml of tetrahydrofuran was stirred at 60° C. for 1 hour.

The reaction mixture was diluted with water, neutralized with 1N hydrochloric acid and extracted with ethyl acetate. The extracts were washed with water, dried and concentrated. The residue was chromatographed on a column of silica gel, elution being conducted with isopropyl ether to obtain 2.4 g (yield: 92.1%) 3-[4-(6-carboxyhex-1-enyl)phenyl]-5-methoxy-2,2,4,6,7-pentamethyl-2,3-dihydrobenzofuran (a mixture of E- and Z-forms).

Reference Example 17

To 10 ml of dimethylformamide was added 1.0 g (3.1 mmol) of 3-(4-formylphenyl)-5-methoxy-2,2,4,6,7-pentamethyl-2,3-dihydrobenzofuran, obtained in Reference Example 11, 0.7 g (3.1 mmol) of triethylphosphonoacetate and 0.15 g (3.75 mmol) of sodium hydride (content: 60 w/w %), which was stirred for 30 min.

The reaction mixture was diluted with water and extracted with ethyl acetate. The extracts were washed with water, dried and concentrated.

Crystallization of the residue from hexane gave 0.7 g (yield: 57.1%) of 3-[4-[2-(ethoxycarbonyl)ethenyl]-phenyl]-5-methoxy-2,2,4,6,7-pentamethyl-2,3-dihydrobenzofuran.

Reference Example 18

2.5 g (5.92 mmol) of 3-[4-(6-carboxyhex-1-enyl)-phenyl]-5-methoxy-2,2,4,6,7-pentamethyl-2,3-dihydrobenzofuran, obtained in Reference Example 16, was hydrogenated by using a 5% palladium-carbon as a catalyst in 20 ml of acetic acid. After filtering out the catalyst, the filtrate obtained was evaporated.

Recrystallization of the residue from isopropyl ether-hexane gave 2.4 g (yield: 95.5%) of 3-[4-(6-carboxyhexyl)phenyl]-5-methoxy-2,2,4,6,7-pentamethyl-2,3-dihydrobenzofuran.

mp. 88°–89° C.

According to the same manner as above, 3-[4-[2-(ethoxycarbonyl)ethyl]phenyl]-5-methoxy-2,2,4,6,7-pentamethyl-2,3-dihydrobenzofuran was obtained from 3-[4-[2-(ethoxycarbonyl)ethenyl]phenyl]-5-methoxy-2,2,4,6,7-pentamethyl-2,3-dihydrobenzofuran. Yield: 90.0%

Reference Example 19

In 10 ml of tetrahydrofuran, was dissolved 1.6 g (3.95 mmol) of 3-(4-bromophenyl)-5-methoxymethyloxy-2,2,4,6,7-pentamethyl-2,3-dihydrobezofuran, obtained in Reference Example 10, to which was added 2.5 ml of 1.6M n-butyl lithium-hexane solution (the content of n-butyl lithium: 4.00 mmol) at −78° C.

The reaction solution was poured into dry-ice which was crushed and made weakly acid with 1N hydrochloric acid, then extracted with ethyl acetate. The extracts were washed, dried and concentrated.

Crystallization of the residue from hexane gave 0.55 g (yield: 38.7%) of 3-(4-carboxyphenyl)-5-methoxymethyloxy-2,2,4,6,7-pentamethyl-2,3-dihydrobenzofuran.

mp. 152°–153° C.

Example 1

A solution of 1.0 g (3.04 mmol) of 1-(2,5-dimethoxy-3,4,6-trimethylphenyl)-1-(3-pyridyl)-2-methylpropanol obtained in Reference Example 7 in 4 ml of 47 w/w % hydrobromic acid was refluxed for 1 hour. After cooling to room temperature, the reaction mixture was neutralized with sodium hydrogen carbonate and extracted with ethyl acetate. The extracts were washed with water, dried and concentrated. Addition of isopropyl ether to the residue gave 0.8 g (yield: 83%) of 5-hydroxy-2,2,4,6,7-pentamethyl-3-(3-pyridyl)-2,3-dihydrobenzofuran as crystals.

The physico-chemical constants inclusive of N.M.R. spectrum are shown in Table 5.

In the same manner as in Example 5, the objective compounds of Examples 2 to 5 were produced from phenethyl alcohol derivative obtained in Reference Example 7. The physico-chemical constants inclusive of N.M.R. spectrum are shown in Table 5.

Example 2

A suspension of 3.2 g (9.2 mmol) of 1-(4-fluorophenyl)-1-(2,5-dimethoxy-3,4,6-trimethylphenyl)-2-methylpropanol, obtained in Reference Example 8, in 15 ml of 47 w/w % hydrobromic acid was refluxed in an atmosphere of argon for 18 hours. After cooling to room temperature, the reaction mixture was diluted with water and extracted with isopropyl ether. The extracts were washed with water, dried and evaporated to remove the solvent.

The residue was chromatographed on a column of silica gel, the elution being conducted with hexane-isopropyl ether (2:1 w/w), and the product obtained was recrystallized from hexane to obtain 2.2 g (yield: 74.8%) of 5-hydroxy-3-(4-fluorophenyl)-2,2,4,6,7-pentamethyl-2,3-dihydrobenzofuran.

The physico-chemical constants inclusive of N.M.R. spectrum are shown in Table 5.

in the manner of Example 5, the objective compounds of Examples 6 to 23 were produced from phenethyl alcohol derivatives obtained in Reference Examples 6 and 8.

Example 3

A solution of 0.5 g of 3-[(2,5-dimethoxy-3,4,6-trimethylphenyl)cyclohexylidenemethyl]pyridine, obtained in Reference Example 9, in 4 ml of 47 w/w % hydrobromic acid was refluxed for 1 hour. After cooling to room temperature, the reaction mixture was neutralized with sodium hydrogen carbonate and extracted with ethyl acetate. The extracts were washed with water, dried and evaporated.

To the residue was added isopropyl ether to obtain 0.4 g (yield: 87.5%) of 5-hydroxy-4,6,7-trimethyl-3-(3-pyridyl)-3H-benzofuran-2-spirocyclohexane.

mp. 186°–187° C.

The physico-chemical constants were shown in Table 5.

According to the same manner as in Example 1, the above objective compound was obtained from 2,5-dimethoxy-3,4,6-trimethylphenyl-(3-pyridyl)cyclohexylmethanol.

Yield: 88%

According to the same manner as above, the compounds of Examples 24 to 39 were obtained, as shown in Table 5. NMR spectra were measured with 100 MHz using CDCl$_3$ as the solvent, unless otherwise specified.

The symbols in Table 5 have the following meanings. 2-Py: 2-pyridyl, 3-Py: 3-pydidyl, Ph: phenyl, Me: methyl, Et: ethyl, Pr: propyl, iPr: isopropyl, Am: amyl, Oc: octyl, Bz: benyl, tBu: tert-butyl, Ind: indanyl, H4Nap: 1,2,3,4-4H-naphthyl, Cyh: cyclohexyl, Nap: naphthyl, Dec: decyl, Dod: dodecyl, Tetd: tetradecyl, Hexd: hexadecyl, Octd: octadecyl.

TABLE 5

| Ex. No. | $R^1$ | $R^2$ | $R^3$ | $R^4$ | $R^5$ | yield (%) | m.P. (°C.) | NMR (δppm) |
|---|---|---|---|---|---|---|---|---|
| 1 | Me | Me | Me | Me | 3-Py | 83.0 | 174–176 | 1.00(3H),1.50(3H),1.80(3H), 2.18(6H),4.10(1H),4.70(1H), 7.17(2H),8.33(1H),8.43(2H) |
| 2 | Me | Me | —(CH$_2$)$_4$— | | 3-Py | 84.0 | 179–180 | 1.00–2.00(8H),1.83(3H), 2.17(6H),4.15(2H),5.20(1H), 7.17(2H),8.40(2H) |
| 3 | Me | Me | —(CH$_2$)$_5$— | | 3-Py | 85.4 | 186–187 | 1.00–2.00(10H),1.80(3H), 2.20(6H),4.03(1H),5.20(1H), 7.13(2H),8.40(2H) |
| 4 | Me | Me | Me | Me | 2-Py | 96.0 | 139–140 | 1.00(3H),1.47(3H),1.80(3H), 2.20(6H),4.30(1H),4.83(1H), 6.73(1H),7.13(1H),7.50(1H), 8.53(1H) |
| 5 | —CH=CH—CH=CH— | | Me | Me | 3-Py | 64.5 | 224–227 | 1.10(3H),1.58(3H),1.97(3H), 3.30(1H),4.50(1H),7.10–7.50(3H),7.80(1H),8.15(1H), 8.40(2H)(DMSO—d$_6$) |
| 6 | Me | Me | Me | Me | Ph | 91.0 | 129–130 | 1.00(3H),1.48(3H),1.80(3H), 2.17(6H),4.08(1H),4.10(1H), 6.93(2H),7.20(3H) |
| 7 | Me | Me | Me | Me | 4-F—Ph | 74.8 | 132–133 | 1.00(3H),1.47(3H),1.80(3H), 2.17(6H),4.07(1H),4.10(1H), 6.80–7.10(4H) |
| 8 | Me | Me | Me | (CH$_2$)$_4$Me (2,3-anti) | 4-F—Ph | 62.2 | 104–105 | 0.87(3H),0.93(3H),1.20–1.70(8H),1.77(3H),2.17(6H), 4.10(1H),4.13(1H),6.90(4H) |
| 9 | Me | Me | Me | Bz (2,3-anti) | 4-F—Ph | 63.1 | 156–157 | 0.86(3H),1.80(3H),2.20(6H), 2.76(1H),3.17(1H),4.13(1H), 4.23(1H),6.85(4H),7.23(5H) |
| 10 | —CH=CH—CH=CH— | | Me | Me | 4-F—Ph | 64.3 | 118–122 | 1.10(3H),1.57(3H),1.93(3H), 4.27(1H),4.93(1H),6.90(4H), 7.40(2H),8.05(2H) |
| 11 | Me | Me | Me | Me | 4-Br—Ph | 87.0 | 113–114 | 1.00(3H),1.47(3H),1.80(3H), 2.17(6H),4.03(1H),4.13(1H), 6.80(2H),7.37(2H) |
| 12 | Me | Me | —(CH$_2$)$_4$— | | 4-Br—Ph | 42.5 | 135–139 | 1.20–2.10(8H),1.83(3H), 2.17(6H),4.07(1H),4.10(1H), 6.87(2H),7.37(2H) |
| 13 | Me | Me | Me | Me | 4-Cl—Ph | 83.5 | 112–113 | 1.00(3H),1.47(3H),1.80(3H), 2.17(6H),4.07(1H),4.10(1H) 6.87(2H),7.22(2H) |
| 14 | Me | Me | Me | Me | 4-CF$_3$—Ph | 81.0 | 116–117 | 1.00(3H),1.50 (3H),1.80(3H), 2.17(6H),4.10(1H),4.13(1H), 7.05(2H),7.50(2H) |
| 15 | Me | Me | Me | Me | 2-F—Ph | 61.7 | 120–121 | 1.05(3H),1.50(3H),1.80(3H), 2.17(3H),4.10(1H),4.53(1H), 6.60(1H),6.80–7.30(3H) |
| 16 | Me | Me | Me | Me | 3-F—Ph | 63.1 | 82–83 | 1.00(3H),1.47(3H),1.80(3H), 2.17(6H),4.07(1H),4.10(1H), 6.50–7.00(3H),7.00–7.40 (1H) |
| 17 | Me | Me | Me | Me | 4-Me—Ph | 93.5 | 113–114 | 1.00(3H),1.47(3H),1.80(3H), 2.20(6H),2.28(3H),4.07(1H), 4.10(1H),6.83(2H),7.05(2H) |
| 18 | Me | Me | Me | Me | 4-Et—Ph | 81.0 | 81–82 | 1.00(3H),1.18(3H),1.47(3H), 2.17(6H),2.60(2H),4.07(1H), 4.10(1H),6.83(2H),7.05(2H) |
| 19 | Me | Me | Me | Me | 4-Pr—Ph | 91.4 | 81–82 | 0.90(3H),1.47(3H),1.60(2H), 1.80(3H),2.17(6H),2.53(2H), 4.05(1H),4.08(1H),6.83(2H), 7.05(2H) |
| 20 | Me | Me | Me | Me | 4-iPr—Ph | 86.8 | 106–107 | 1.00(3H),1.17(3H),1.25 (3H), 1.80(3H),2.17(6H),2.83(1H), 4.07(1H),4.10(1H),6.83(2H), 7.05(2H) |
| 21 | Me | Me | Me | Me | 4-tBu—Ph | 86.0 | oil | 1.00(3H),1.27(9H),1.47(3H), |

TABLE 5-continued

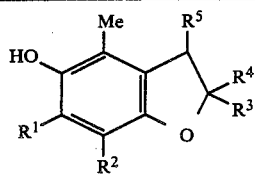

| Ex. No. | $R^1$ | $R^2$ | $R^3$ | $R^4$ | $R^5$ | yield (%) | m.P. (°C.) | NMR (δppm) |
|---|---|---|---|---|---|---|---|---|
| 22 | Me | Me | Me | Me | 4-Am-Ph | 78.5 | 78–79 | 1.80(3H),2.17(6H),4.07(1H), 4.10(1H),6.83(2H),7.23(2H) 0.87(3H),1.00(3H),1.30(6H), 1.48(3H),1.50(2H),1.82(3H), 2.20(6H),2.57(2H),4.07(1H), 4.10(1H),6.83(2H),7.05(2H) |
| 23 | Me | Me | Me | Me | 4-Oc-Ph | 89.3 | 44–45 | 0.90(3H),1.00(3H),1.27(12H) 1.47(3H),1.50(2H),1.80(3H), 2.17(6H),2.53(2H),4.05(1H), 4.08(1H),6.83(2H),7.05(2H) |
| 24 | Me | Me | Me | Me | 4-Dec-Ph | 95.5 | 61–62 | 0.87(3H),0.97(3H),1.23(14H) 1.45(3H),1.50(2H),1.80(3H), 2.15(6H),2.53(2H),4.07(2H), 6.80(2H),7.03(2H) |
| 25 | Me | Me | Me | Me | 4-Dod-Ph | 78.5 | 69–70 | 0.87(3H),0.97(3H),1.23(18H) 1.45(3H),1.50(2H),1.80(3H), 2.15(6H),2.53(2H),4.07(2H), 6.80(2H),7.03(2H) |
| 26 | Me | Me | Me | Me | 4-Tetd-Ph | 75.5 | 73–74 | 0.87(3H),0.97(3H),1.23(22H) 1.45(3H),1.50(2H),1.80(3H), 2.15(6H),2.53(2H),4.07(2H), 6.80(2H),7.03(2H) |
| 27 | Me | Me | Me | Me | 4-Hexd-Ph | 86.6 | 76–77 | 0.87(3H),0.97(3H),1.23(26H) 1.45(3H),1.50(2H),1.80(3H), 2.15(6H),2.53(2H),4.07(2H), 6.80(2H),7.03(2H) |
| 28 | Me | Me | Me | Me | 4-Octd-Ph | 84.9 | 70–71 | 0.87(3H),0.97(3H),1.23(3OH) 1.45(3H),1.50(2H),1.80(3H), 2.15(6H),2.53(2H),4.07(2H), 6.80(2H),7.03(2H) |
| 29 | Me | Me | Me | Me | 4-OH—Ph | 67.6 | 246–248 | (DMSO—$d_6$) 0.90(3H),1.37(3H),1.73(3H), 2.03(3H),2.07(3H),3.98(1H, 6.67(4H),7.27(1H),9.10(1H) |
| 30 | Me | Me | Me | Me | 3-OH—Ph | 57.4 | 132–133 | 1.03(3H),1.47(3H),1.82(3H), 2.13(6H),4.02(1H),4.13(1H), 4.87(1H),6.20–6.70(3H), 7.10(1H) |
| 31 | Me | Me | Me | Me | 4-MeS—Ph | 83.4 | 132–133 | 1.00(3H),1.45(3H),1.80(3H), 2.15(6H),2.43(3H),4.03(1H), 4.10(1H),6.83(2H),7.12(2H) |
| 32 | Me | Me | Me | Me | 2,4-diMe—Ph | 85.6 | 101–102 | 1.00(3H),1.48(3H),1.73(3H), 2.17(6H),2.23(3H),2.37(3H), 4.07(1H),4.33(1H),6.40(1H), 6.80(1H),6.95(1H) |
| 33 | Me | Me | Me | Me | 3,4-diMe—Ph | 95.1 | 118–119 | 1.00(3H),1.45(3H),1.80(3H), 2.17(9H),2.20(3H),4.03(1H), 4.10(1H),6.70(2H),6.97(1H) |
| 34 | Me | Me | Me | Me | 5-Ind | 95.8 | 108–109 | 1.00(3H),1.45(3H),1.82(3H), 2.00(2H),2.17(6H),2.83(4H), 4.05(1H),4.08(1H),6.73(2H), 7.07(1H) |
| 35 | Me | Me | Me | Me | 6-H$_4$Nap | 82.8 | 115–116 | 0.93(3H),0.97(3H),1.73(4H), 2.10(3H),2.17(3H),2.43(3H), 2.70(4H),2.80(1H),3.03(3H), 3.60(3H),6.27(1H),6.90(1H), 7.10(2H) |
| 36 | Me | Me | Me | Me | 4-Cyh | 95.4 | 117–118 | 1.00(3H),1.20–2.00(10H), 1.47(3H),180(3H),2.17(3H), 4.05(1H),4.08(1H),6.82(2H), 7.05(2H) |
| 37 | Me | Me | Me | Me | 1-Nap | 94.2 | 158–159 | 0.90(3H)1.65(3H),1.70(3H), 2.20(6H),4.13(1H),5.00(1H), 6.73(1H),7.20–8.20(6H) |
| 38 | Me | Me | Me | Me | 2-Nap | 89.6 | 147–148 | 1.00(3H),1.53(3H),1.77(3H), 2.20(6H),4.10(1H),4.27(1H), 7.03(1H),7.40(3H),7.73(3H) |
| 39 | Me | Me | Me | Me | 4-Me$_2$N—Ph | 96.4 | 119–120 | 1.00(3H),1.43(3H),1.82(3H), 2.15(6H),2.88(6H),4.02(1H), |

TABLE 5-continued

[Structure: benzofuran with HO, Me, R⁵, R⁴, R³, R¹, R² substituents]

| Ex. No. | R¹ | R² | R³ | R⁴ | R⁵ | yield (%) | m.P. (°C.) | NMR (δppm) |
|---|---|---|---|---|---|---|---|---|
| | | | | | | | | 4.07(1H),6.60(2H),6.78(2H) |

Example 40

To a solution of 0.5 g (1.66 mmol) of 3-(4-fluorophenyl)-5-hydroxy-2,2,4,6,7-pentamethyl-2,3-dihydrobenzofuran, obtained in Example 7, in 5 ml of dimethylformamide was added 80 mg (20 mmol) of sodium hydride (content: 60 w/w %), and the mixture was stirred for 30 min. To the reaction mixture was added 156 mg (20 mmol) of acetyl chloride, and stirred at room temperature for 30 min.

To the reaction mixture was added water. This was followed by extraction with isopropyl ether. The extracts were washed with water, dried and evaporated. Recrystallization of the obtained residue from hexane gave 0.4 g (yield: 70.2%) of 5-acetoxy-3-(4-fluorophenyl)-2,2,4,6,7-pentamethyl-2,3-dihydrobenzofuran.

mp. 86°–87° C.

NMR (δ ppm) CDCl₃ 1.00(3H), 1.50(3H), 1.67(3H), 2.07(3H), 2.17(3H), 2.27(3H), 4.13(1H), 6.93(4H)

In the same manner as above, the compounds of Examples 41 to 45 were obtained, as shown in Table 6.

NMR spectra were measured with 90 MHz using CDCl₃ as the solvent, unless otherwise specified.

The symbols in Table 6 have the following meanings. iPr: isopropyl, Cyh: cyclohexyl, Non: nonyl, Ph: phenyl, Nicoty: nicotinyl.

TABLE 6

[Structure: benzofuran with R⁰O, Me, R⁵, Me, Me, Me, Me substituents]

| Ex. No. | R⁰ | R⁵ | yield (%) | m.p. (°C.) | NMR(δ ppm) |
|---|---|---|---|---|---|
| 41 | iPrCO | 4-F—Ph | 89.2 | 98–99 | 1.00(3H), 1.27(3H), 1.33(3H), 1.48(3H), 1.63(3H), 2.03(3H), 2.17(3H), 2.80(1H), 4.10(1H), 6.90(4H) |
| 42 | CyhCO | 4-F—Ph | 58.5 | 107–108 | 1.00(3H), 1.50(3H), 1.10–2.20(10H), 1.63 (3H), 2.03(3H), 2.17(3H), 2.55(1H), 4.10(1H), 6.93(4H) |
| 43 | NoNCO | 4-F—Ph | 92.6 | 61–62 | 0.87(3H), 0.98(3H), 1.27(12H), 1.48(3H), 1.63(3H), 1.73(2H), 2.03(3H), 2.13(3H), 2.53 (2H), 4.10(1H), 6.97(4H) |
| 44 | PhCO | 4-F—Ph | 81.7 | 146–147 | 1.00(3H), 1.50(3H), 1.70(3H), 2.07(3H), 2.17(3H), 4.13(1H), 6.93(4H), 7.56(3H), 8.20(2H) |
| 45 | Nicoty | 4-F—Ph | 66.7 | 140–141 | 1.03(3H), 1.50(3H), 1.70(3H), 2.10(3H), 2.20(3H), 4.15(1H), 6.97(4H), 7.45(1H) 8.47(1H), 8.87(1H), 9.45(1H) |

Example 46

A solution of 1.0 g (3.5 mmol) of 5-hydroxy-2,2,4,6,7-pentamethyl-3-(3-pyridyl)-2,3-dihydrobenzofuran, obtained in Example 1, in 3 ml of methyl iodide was left to stand at room temperature for 2 hours. The precipitating crystals which were filtered, and washed with isopropyl ether to obtain 1.4 g (yield: 94%) of 5-hydroxy-2,2,4,6,7-pentamethyl-3-(1-methyl-3-pyridinio)-2,3-dihydrobenzofuran iodide as crude ctystals.

Recrystallization of the crude crystals from ethanolethyl acetate gave the objective compound melting at 168°–169° C.

NMR (δ ppm) CDCl₃ 1.00(3H), 1.47(3H), 1.77(3H), 2.08(3H), 2.10(3H), 4.40(3H), 4.50(1H), 7.50(1H), 8.00(2H), 8.90(2H)

Example 47

According to the same manner as in Example 46, from 0.38 (0.74 mmol) of 3-(4-fluorophenyl)-2,2,4,6,7-pentamethyl-5-nicotinyloxy-2,3-dihydrobenzofuran, 0.3 g (yield: 74%) of 3-(4-fluorophenyl)-2,2,4,6,7-pentamethyl-5-[(1-methyl-3-pyridinio)carboxy]-2,3-dihydrobenzofuran iodide was obtained.

mp. 227°–230° C.

NMR (δ ppm) CDCl₃ 1.00(3H), 1.50(3H), 1.70(3H), 2.07(3H), 2.17(3H), 4.40(1H), 4.50(3H), 7.10(4H), 8.37(1H), 9.25(2H), 9.88(1H)

Example 48 a solution of 3.0 g (9.3 mmol) of 3-(4-formylphenyl)-5-methoxy-2,2,4,6,7-pentamethyl-2,3-dihydrobenzofuran in 30 ml of 48 w/w % hydrobromic acid was refluxed for 3 hours. After cooling to room temperature, the reaction mixture was diluted with water, and extracted with isopropyl ether. The extracts were washed with water and a saturated aqueous sodium hydrogen carbonate in that order, then dried and concentrated.

Crystallization of the residue from hexane-isopropyl ether gave 1.4 g (yield: 48.8%) of 3-(4-formylphenyl)-5-hydroxy-2,2,4,6,7-pentamethyl-2,3-dihydrobenzofuran. The physico-chemical constants are shown in Table 7.

According to the same demethylation and demethoxylation as above, the compounds of Examples 49, 53, 54 and 55 were produced.

By subjecting nitrile or ester to hydrolysis at the same time following the same manner as above, the compounds of Examples 50, 51 and 52 were obtained.

NMR spectra were measured with 90 MHz using CDCl₃ as the solvent, unless otherwise specified.

The symbols in Table 7 have the following meanings.
Ph: phenyl, Pipe: piperidino.

NMR (δ ppm) CDCl₃ 1.00(3H), 1.50(3H), 1.80(3H), 2.00(1H), 2.20(6H), 4.10(1H), 4.15(1H), 4.63(2H), 6.95(2H), 7.25(2H)

Example 57

To a solution of 1.5 g (4.25 m mol) of 4-(5-hydroxy-2,2,4,6,7-pentamethyl-2,3-dihydrobenzofuran-3-yl)cinnamic acid obtained in Example 51 in 10 ml of ethanol was added 0.1 ml of sulfuric acid and the solution was refluxed for 5 hours. After cooling, the reaction mixture was diluted with water and extracted with ethyl acetate. The extracts were washed with aqueous saturated sodium bicarbonate, dried and concentrated. Addition of isopropyl ether-hexane to the residue gave 1.2 g (yield: 73.9%) of ethyl 4-(5-hydroxy-2,2,4,6,7-pentamethyl-2,3-dihydrobenzofuran-3-yl)cinnmate mp. 119°–120° C.

NMR (δ ppm) CDCl₃ 1.00(3H), 1.30(3H), 1.47(3H),

TABLE 7

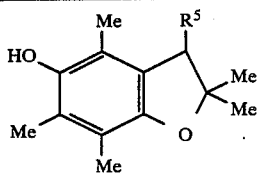

| Ex. No. | R⁵ | yield (%) | m.p. (°C.) | NMR(δ ppm) |
|---|---|---|---|---|
| 48 | 4-CHO—Ph | 48.8 | 139–140 | 1.00(3H), 1.50(3H), 1.77(3H), 2.17(3H), 4.17(1H), 4.20(1H), 7.10(2H), 7.77(2H), 9.97(1H) |
| 49 | 4-CO₂H—Ph | 82.9 | 218–220 | 1.00(3H), 1.48(3H), 1.78(3H), 2.17(6H), 4.17(1H), 4.70(2H), 7.05(2H), 7.98(2H) |
| 50 | 4-CH₂CO₂H—Ph | 88.0 | oil | 1.00(3H), 1.47(3H), 1.77(3H), 2.17(6H), 3.57(2H), 4.07(1H), 6.87(2H), 7.17(2H), 7.90(2H) |
| 51 | 4-CH=CH—CO₂H—Ph | 83.4 | 215–220 | (DMSO—d₆) 0.95(3H), 1.43(3H), 1.73(3H), 2.07(3H), 2.10(3H), 4.15(1H), 6.40(1H), 6.97(2H), 7.35(2H), 7.52(2H), 7.53(1H) |
| 52 | 4-(CH₂)₂COOH—Ph | 86.0 | Oil | 0.97(3H), 1.47(3H), 1.80(3H), 2.17(6H), 2.60(2H), 2.90(2H), 4.07(1H), 6.00(2H), 6.83(2H), 7.07(2H) |
| 53 | 4-(CH₂)₆COOH—Ph | 83.0 | Oil | 1.00(3H), 1.20–1.80(8H), 1.47(3H), 1.80(3H), 2.13(3H), 2.20(3H), 2.23(2H), 2.57(2H), 4.07(1H), 6.80(2H), 6.90(1H), 7.03(2H), 9.20(2H) |
| 54 | 4-CH₂SPh—Ph | 79.0 | Oil | 0.97(3H), 1.47(3H), 1.80(3H), 2.13(2H), 2.20(3H), 4.05(1H), 4.08(1H), 6.80(2H), 7.05–7.30(7H) |
| 55 | 4-CH₂PiPe—Ph | 58.0 | 234–237 | 0.93(3H), 1.40(3H), 1.73(3H), 1.50–2.00(6H), 2.07(3H), 2.13(3H), 2.70–3.30(4H), 4.17(3H), 6.95(2H), 7.53(2H) |

1.80(3H), 2.17(6H), 4.12(1H), 4.25(2H), 6.37(1H), 6.95(2H), 7.40(2H), 7.65(2H)

Example 56

To a solution of 1.0 g (3.2 mmol) of 3-(4-formylphenyl)-5hydroxy-2,2,4,6,7-pentamethyl-2,3-dihydrobenzofuran obtained in Example 48 in 15 ml of ethanol was added 121 mg (3.2 mmol) of sodium borohydride. This was followed by stirring at 0° C. for 30 min. The reaction mixture was diluted with water, and extracted with ethyl acetate. The extracts were washed with water, dried and concentrated.

Crystallization of the residue from isopropyl ether-hexan gave 0.6 g (yield: 59.6%) of 5-hydroxy-3-[4-(hydroxymethyl)phenyl]-2,2,4,6,7-pentamethyl-2,3-dihydrobenzofuran.
mp. 135°–136° C.

Example 58

To a solution of 2.0 g (6.16 m mol) of 5-hydroxy-2,2,4,6,7-pentamethyl-3-(4-isopropylphenyl)-2,3-dihydrobenzofuran obtained in Example 20 in 10 ml of dibutyl ether were added 740 mg (7.4 m mol) of anhydrous succinic acid and 0.1 ml of conc. sulfuric acid. This was stired at 80° C. for 1 hour. After cooling, the reaction mixture was washed with water, dried and concentrated. The resulting residue was purified by silica gel chromatography (eluted by isopropyl ether). Addition of isopropyl ether-hexane to the resulting concentrate gave 620 mg (yield 23.7%) of 3[3-(4-isopropylphenyl)-2,2,4,6,7-pentamethyl-2,3-dihydrobenzofuran-5-yloxycarbonyl]propionic acid. mp. 141°–142° C.

Example 59

To a solution of 1.0 g (3.53 m mol) of 5-hydroxy-2,2,4,6,7-pentamethyl-3-(3-pyridyl)-2,3-dihydrobenzofuran obtained in Example 1 in 10 ml of ethanol was added 0.5 ml of conc. hydrochloric acid. The reaction mixture was concentrated. To the residue was added a small amount of ethyl acetate. The resulting crystals were collected by filtration, washed with ethyl acetate and gave 1.02 g (yield 90.5%, containing an equivalent mole of ethyl acetate as solvent of crystallization) of 5-hydroxy-2,2,4,6,7-pentamethyl-3-(3-pyridyl)2,3-dihydrobenzofuran hydrochloride. mp. 202°–205° C.

In the same manner as above, 5-hydroxy-2,2,4,6,7-pentamethyl-3-(4-dimethylaminophenyl)-2,3-dihydrobenzofuran hydrochloride (yield 93.6%, mp. 225°–228° C.) from the corresponding free compound obtained in Example 39.

What is claimed is:

1. A compound of the formula

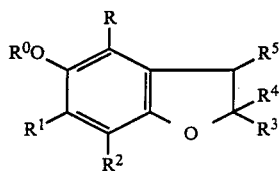

wherein

R is a $C_{1-6}$ alkyl group;

$R^o$ is (1) hydrogen, (2) a $C_{1-10}$ alkanoyl group which may optionally be substituted by carboxyl, (3), a $C_{3-7}$ cycloalkyl-carbonyl group, (4) a $C_{6-14}$ arylcarbonyl group, (5) a pyridinecarbonyl group which may optionally be substituted by $C_{1-6}$ alkyl or phenyl and which may be made quaternary or (6) a sulfonic acid or phosphoric acid acyl which contains as a substituent a $C_{1-6}$ alkyl or phenyl group;

$R^1$ and $R^2$ each are a $C_{1-6}$ alkyl group which may optionally be substituted by 1 to 3 hydroxy, halogen, nitro, trifluoromethyl, carboxy, $C_{1-3}$ alkoxycarbonyl, 3-pyridyl, 1-imidazolyl or 5-thiazolyl groups, or wherein $R^1$ and $R^2$ are combined to form a benzene or naphthalene ring which may optionally be substituted by 1 to 3 $C_{1-3}$ alkyl, $C_{1-3}$ alkoxy, hydroxy, nitro or halogen groups;

$R^3$ and $R^4$ each are hydrogen or a $C_{1-20}$ alkyl group which may optionally be substituted by 1 to 5 groups of the class consisting of (1) hydroxy, (2) carboxy, (3) $C_{1-4}$ alkoxycarbonyl groups or (4) $C_{6-14}$ aryl groups which may optionally be substituted by 1 to 5 hydroxy, $C_{1-3}$ alkyl, halogen, $C_{1-3}$ alkoxy, carboxy, trifluoromethyl, 3-pyridyl, 1-imidazolyl or 5-thiazolyl groups, or wherein $R^3$ and $R^4$ are combined to form a $C_{2-5}$ alkylene group;

$R^5$ is a pyridyl, 1-imidazolyl or 5-thiazolyl group, which may optionally be made quaternary at the ring-constituting nitrogen atom with a $C_{1-3}$ alkyl group, a thienyl group or a phenyl, 1- or 2-naphthyl, indanyl or tetralyl group, in which groups each may optionally be substituted by 1 to 5 groups the class consisiting of (1) $C_{1-20}$ alkyl, (2) $C_{1-6}$ alkyl which is substituted by hydroxy, carboxy, $C_{1-4}$ alkoxycarbonyl, piperidinyl or phenylthio, (3) $C_{2-4}$ alkenyl which may be substituted by carboxy or $C_{1-6}$ alkoxycarbonyl, (4) hydroxy, (5) halogen, (6) formyl, (7) $C_{1-3}$ alkoxy, (8) carboxy, (9) trifluoromethyl, (10) di-$C_{1-3}$ alkylamino, (11) $C_{5-7}$ cycloalkyl or (12) $C_{1-3}$ alkylthio groups, or a pharmaceutically acceptable salt thereof.

2. A compound as claimed in claim 1, wherein R is a straight-chain or branched $C_{1-6}$ alkyl group.

3. A compound as claimed in claim 1, wherein $R^o$ is hydrogen or a $C_{1-10}$ alkanoyl group which may optionally be substituted by carboxy.

4. A compound as claimed in claim 1, wherein $R^o$ is a $C_{3-7}$ cycloalkylcarbonyl group, $C_{8-14}$ arylcarbonyl group or pyridinecarbonyl group which may optionally be substituted by $C_{1-6}$ alkyl.

5. A compound as claimed in claim 1, wherein $R^1$ and $R^2$ are straight-chain or branched $C_{1-6}$ alkyl groups, or $R^1$ and $R^2$ are combined to form a benzene ring.

6. A compound as claimed in claim 1, wherein $R^3$ and $R^4$ are $C_{1-20}$ alkyl groups which may optionally be substituted by hydroxy or carboxy, or $R^3$ and $R^4$ are combined to form a $C_{2-5}$ alkylene group.

7. A compound as claimed in claim 1, wherein $R^5$ is pyridyl which may optionally be made quaternary, or a phenyl, 1-or 2-naphthyl, indanyl or tetralyl group which groups may optionally be substituted by (1) a straight-chain or branched $C_{1-6}$ alkyl group which may optionally be substituted by carboxy, hydroxy, halogen, phenylthio or piperidinyl, the number of the substituents being 1 to 3, (2) a $C_{5-6}$ cycloalkyl group, (3) a $C_{2-4}$ alkenyl group which may be substituted by carboxy, (4) hydroxy, (5) halogen, (6) formyl, (7) carboxy, (8) a di-$C_{1-3}$ alkylamino group or (9) a $C_{1-3}$ alkylthio group, the number of the substituents being 1 to 3.

8. A compound as claimed in claim 1, wherein $R^3$ and $R^4$ are straight-chain or branched $C_{1-6}$ alkyl groups which may optionally be substituted by a $C_{6-14}$ aryl group, or $R^3$ and $R^4$ are combined to form a butylene or pentylene group.

9. A compound as claimed in claim 1, wherein R is methyl, $R^o$ is hydrogen, a $C_{1-10}$ alkanoyl group nicotinoyl; $R^1$ and $R^2$ are methyl or $R^1$ and $R^2$ are combined to form butadienylene; $R^3$ is methyl; $R^4$ is methyl, pentyl or benzyl or $R^3$ and $R^4$ are combined to form butylene or pentylene; and $R^5$ is (1) phenyl which may be substituted by a straight-chain or branched $C_{1-10}$ alkyl group, halogen, hydroxy or trifluoromethyl, the number of the substituents being 1 to 3, or (2) 2- or 3-pyridyl.

10. The compound as claimed in claim 1, which is 5-hydroxy-2,2,4,6,7-pentamethyl-3-(4-isopropylphenyl)-2,3-dihydrobenzofuran.

11. The compound as claimed in claim 1, which is 5-hydroxy-2,2,4,6,7-pentamethyl-3-(4-fluorophenyl)2,3-dihydrobenzofuran.

12. The compound as claimed in claim 1, which is 5-hydroxy-2,2,4,6,7-pentamethyl-3-[4-(2-carboxyethenyl)phenyl]-2,3-dihydrobenzofuran.

13. The compound as claimed in claim 1, which is 5-hydroxy-2,2,4,6,7-pentamethyl-3-(5,6,7,8-tetrahydro-2-naphthyl)-2,3-dihydrobenzofuran.

14. The compound as claimed in claim 1, which is 5-hydroxy-2,2,4,6,7-pentamethyl-3-(4octylphenyl)-2,3-dihydrobenzofuran.

15. An antithrombotic, anti-vasoconstrictive, antiallergic, antinephritic, anti-fibrositic, active oxygen-elminating and arachidonate cascade control improving agent comprising an effective dose for such use of a compound of claim 1 or a pharmaceutically acceptable salt thereof and a pharmaceutically acceptable carrier or excipient.

16. A method of treating neuronal degeneration, memory impairment, spinal injury, and neurological deficits, which comprises administering to a mammal in need thereof an effective amount of a compound or pharmaceutically acceptable salt thereof as defined in claim 1.

* * * * *